United States Patent
Boehringer et al.

(10) Patent No.: US 7,951,124 B2
(45) Date of Patent: May 31, 2011

(54) GROWTH STIMULATING WOUND DRESSING WITH IMPROVED CONTACT SURFACES

(75) Inventors: John R. Boehringer, Wynnewood, PA (US); John Karpowicz, Chester Springs, PA (US); Amitabha Mitra, Voorhees, NJ (US); Christopher L. Radl, Malvern, PA (US)

(73) Assignee: Boehringer Technologies, LP, Phoenixville, PA (US)

( * ) Notice: Subject to any disclaimer, the term of this patent is extended or adjusted under 35 U.S.C. 154(b) by 252 days.

(21) Appl. No.: 11/825,397

(22) Filed: Jul. 6, 2007

(65) Prior Publication Data

US 2008/0177253 A1    Jul. 24, 2008

Related U.S. Application Data

(63) Continuation-in-part of application No. 10/982,346, filed on Nov. 5, 2004, now Pat. No. 7,884,258.

(60) Provisional application No. 60/819,146, filed on Jul. 7, 2006.

(51) Int. Cl.
*A61M 1/00* (2006.01)
(52) U.S. Cl. .......................................... 604/319; 602/43
(58) Field of Classification Search .................. 604/304, 604/319, 19, 317, 540, 543; 602/42–48; 424/443
See application file for complete search history.

(56) References Cited

U.S. PATENT DOCUMENTS

| | | |
|---|---|---|
| 2,122,121 A | 6/1938 | Tillotson |
| 2,385,207 A | 9/1945 | Hunn |
| 3,042,037 A | 7/1962 | Scales et al. |
| 3,053,252 A | 9/1962 | Wolf |
| 3,307,545 A | 3/1967 | Surowitz |
| 3,568,675 A | 3/1971 | Harvey |
| 3,602,220 A | 8/1971 | Bunyan |
| 3,616,156 A | 10/1971 | Scholl |

(Continued)

FOREIGN PATENT DOCUMENTS

DE    2 161 235    7/1973

(Continued)

OTHER PUBLICATIONS

Chariker, et al., Effective Management of Incisional and Cutaneous Fistulae with Closed Suction Wound Drainage, *Contemporary Surgery*, vol. 34, Jun. 1989, pp. 59-63.

(Continued)

*Primary Examiner* — Leslie R Deak
*Assistant Examiner* — Benedict L Hanrahan
(74) *Attorney, Agent, or Firm* — Caesar, Rivise, Bernstein, Cohen & Pokotilow, Ltd.

(57) ABSTRACT

A wound contact device comprising a permeable material and a wound contact layer having voids extending through the contact layer to a depth in the permeable material. The wound contact layer can comprise a thin sheet or film forming a generally flat and smooth wound contact surface having essentially no discontinuities or gaps. The wound contact layer can comprise a thin sheet of highly calendered fabric forming a wound contact surface having a mean surface roughness in the range of about 0 microns to about 200 microns. In progressive wound healing, an embodiment of the wound contact device having the fabric contact surface is used in earlier healing stages and an embodiment of the wound contact device with film contact surface is used in later healing stages. The wound contact device is particularly useful in wound dressings for use in suction-assisted wound therapy.

38 Claims, 11 Drawing Sheets

U.S. PATENT DOCUMENTS

| | | | |
|---|---|---|---|
| 3,703,897 A | 11/1972 | Mack et al. | |
| 3,790,433 A | 2/1974 | Baron | |
| 3,870,041 A | 3/1975 | Davies | |
| 3,874,387 A | 4/1975 | Barbieri | |
| 3,929,135 A | 12/1975 | Thompson | |
| 4,180,074 A | 12/1979 | Murry et al. | |
| 4,224,945 A | 9/1980 | Cohen | |
| 4,252,590 A | 2/1981 | Rasen et al. | |
| 4,323,069 A | 4/1982 | Ahr et al. | |
| 4,382,441 A | 5/1983 | Svedman | |
| 4,533,352 A | 8/1985 | Van Beek et al. | |
| 4,542,739 A | 9/1985 | Schafer et al. | |
| 4,906,240 A | 3/1990 | Reed et al. | |
| 4,969,880 A | 11/1990 | Zamierowski et al. | |
| 4,997,425 A | 3/1991 | Shioya et al. | |
| 5,034,006 A | 7/1991 | Hosoda et al. | |
| 5,059,424 A | 10/1991 | Cartmell et al. | |
| 5,100,396 A | 3/1992 | Zamierowski | |
| 5,106,629 A | 4/1992 | Cartmell et al. | |
| 5,147,338 A | 9/1992 | Lang et al. | |
| 5,176,663 A | 1/1993 | Svedman et al. | |
| 5,261,893 A | 11/1993 | Zamierowsk | |
| 5,358,494 A | 10/1994 | Svedman | |
| 5,409,472 A * | 4/1995 | Rawlings et al. | 604/307 |
| 5,437,651 A | 8/1995 | Todd et al. | |
| 5,447,505 A | 9/1995 | Valentine et al. | |
| 5,465,735 A | 11/1995 | Patel | |
| 5,527,213 A | 6/1996 | Tyler et al. | |
| 5,527,293 A | 6/1996 | Zamierowski | |
| 5,549,584 A * | 8/1996 | Gross | 604/313 |
| 5,556,375 A | 9/1996 | Ewall | |
| 5,607,388 A | 3/1997 | Ewall | |
| 5,633,007 A | 5/1997 | Webb et al. | |
| 5,636,643 A | 6/1997 | Argenta et al. | |
| 5,645,081 A | 7/1997 | Argenta et al. | |
| 5,810,756 A | 9/1998 | Montecalvo et al. | |
| 5,919,180 A | 7/1999 | Raimondo | |
| 6,071,267 A | 6/2000 | Zamierowski | |
| 6,126,701 A | 10/2000 | Calogero | |
| 6,203,563 B1 | 3/2001 | Fernandez | |
| 6,207,875 B1 * | 3/2001 | Lindqvist et al. | 602/46 |
| 6,290,685 B1 | 9/2001 | Insley | |
| 6,345,623 B1 | 2/2002 | Heaton et al. | |
| 6,458,109 B1 | 10/2002 | Henley et al. | |
| 6,468,383 B2 | 10/2002 | Kundel | |
| 6,520,982 B1 | 2/2003 | Boynton et al. | |
| 6,626,891 B2 | 9/2003 | Ohmstede | |
| 6,682,757 B1 | 1/2004 | Wright | |
| 6,685,681 B2 | 2/2004 | Lockwood et al. | |
| 6,689,931 B2 | 2/2004 | Etheredge, III | |
| 6,695,823 B1 | 2/2004 | Lina et al. | |
| 6,737,149 B1 | 5/2004 | Wintermantel et al. | |
| 6,752,794 B2 | 6/2004 | Lockwood et al. | |
| 6,755,807 B2 | 6/2004 | Risk, Jr. et al. | |
| 6,764,462 B2 | 7/2004 | Risk, Jr. et al. | |
| 6,767,334 B1 | 7/2004 | Randolph | |
| 6,800,074 B2 | 10/2004 | Henley et al. | |
| 6,855,135 B2 | 2/2005 | Lockwood et al. | |
| 6,885,135 B2 | 4/2005 | Kanao et al. | |
| 6,897,349 B2 | 5/2005 | Gibbins et al. | |
| 6,936,037 B2 | 8/2005 | Bubb et al. | |
| 6,951,553 B2 | 10/2005 | Bubb et al. | |
| 7,070,584 B2 | 7/2006 | Johnson et al. | |
| 7,108,683 B2 | 9/2006 | Zamierwoski | |
| 7,117,869 B2 | 10/2006 | Heaton et al. | |
| 7,198,046 B1 | 4/2007 | Argenta et al. | |
| 7,216,651 B2 | 5/2007 | Argenta et al. | |
| 7,223,899 B2 | 5/2007 | Sigurjonsson | |
| 7,273,054 B2 | 9/2007 | Heaton et al. | |
| 7,338,482 B2 | 3/2008 | Lockwood et al. | |
| 7,494,482 B2 | 2/2009 | Orgill et al. | |
| 7,722,582 B2 | 5/2010 | Lina et al. | |
| 2001/0031943 A1 | 10/2001 | Urie | |
| 2001/0043943 A1 | 11/2001 | Coffey | |
| 2002/0065494 A1 | 5/2002 | Lockwood et al. | |
| 2002/0115952 A1 | 8/2002 | Johnson et al. | |
| 2002/0161346 A1 | 10/2002 | Lockwood et al. | |
| 2003/0040691 A1 | 2/2003 | Griesbach, III et al. | |
| 2003/0093041 A1 | 5/2003 | Risk, Jr. et al. | |
| 2003/0176827 A1 | 9/2003 | Chandra et al. | |
| 2004/0002676 A1 | 1/2004 | Siegwart et al. | |
| 2004/0006319 A1 | 1/2004 | Lina et al. | |
| 2004/0030304 A1 | 2/2004 | Hunt et al. | |
| 2004/0039415 A1 | 2/2004 | Zamierowski | |
| 2004/0054338 A1 | 3/2004 | Rybordi et al. | |
| 2004/0064111 A1 | 4/2004 | Lockwood et al. | |
| 2004/0064132 A1 | 4/2004 | Boehringer et al. | |
| 2004/0093026 A1 | 5/2004 | Weidenhagen et al. | |
| 2004/0122434 A1 | 6/2004 | Argenta et al. | |
| 2004/0127862 A1 | 7/2004 | Bubb et al. | |
| 2004/0127863 A1 | 7/2004 | Bubb et al. | |
| 2005/0004534 A1 | 1/2005 | Lockwood et al. | |
| 2005/0010153 A1 | 1/2005 | Lockwood et al. | |
| 2005/0064021 A1 | 3/2005 | Rippon et al. | |
| 2005/0070858 A1 | 3/2005 | Lockwood et al. | 604/319 |
| 2005/0131327 A1 | 6/2005 | Lockwood et al. | |
| 2005/0209574 A1 | 9/2005 | Boehringer et al. | |
| 2005/0228329 A1 | 10/2005 | Boehringer et al. | |
| 2006/0041247 A1 | 2/2006 | Petrosenko et al. | |
| 2006/0064049 A1 | 3/2006 | Marcussen | |
| 2006/0128245 A1 | 6/2006 | Muth et al. | 442/327 |
| 2006/0129137 A1 | 6/2006 | Lockwood et al. | |
| 2006/0189910 A1 | 8/2006 | Johnson et al. | |
| 2006/0213527 A1 | 9/2006 | Argenta et al. | |
| 2007/0021697 A1 | 1/2007 | Ginther et al. | |
| 2007/0032778 A1 | 2/2007 | Heaton et al. | |
| 2007/0038172 A1 | 2/2007 | Zamierwoski | |
| 2007/0185426 A1 | 8/2007 | Ambrosio et al. | |
| 2007/0219471 A1 | 9/2007 | Johnson et al. | |
| 2007/0219489 A1 | 9/2007 | Johnson et al. | |
| 2007/0219497 A1 | 9/2007 | Johnson et al. | |
| 2007/0219513 A1 | 9/2007 | Lina et al. | |

FOREIGN PATENT DOCUMENTS

| | | |
|---|---|---|
| EP | 0619105 A1 | 10/1994 |
| GB | 2329127 A | 3/1999 |
| WO | WO 80/01139 | 6/1980 |
| WO | WO 91/00718 | 1/1991 |
| WO | WO 00/45761 | 8/2000 |
| WO | 0137922 A3 | 5/2001 |
| WO | WO 01/34079 | 5/2001 |
| WO | 02092783 A2 | 11/2002 |
| WO | 03057071 A2 | 7/2003 |
| WO | WO 03/057070 A2 | 7/2003 |
| WO | WO 03/057070 A3 | 7/2003 |
| WO | WO 2004/037334 A1 | 5/2004 |
| WO | 2005046761 A1 | 5/2005 |
| WO | WO 2005/046762 A1 | 5/2005 |

OTHER PUBLICATIONS

Ko, Frank ; Fabrics, *Encyclopedia of Biomaterials and Biomedical Engineering*, 2004, Draft Copy, pp. 1-38.

Ma, Peter X., Scaffolds for Tissue Fabrication, *Materialstoday*, May 2004, pp. 30-40.

Marois, Yves et al. "Endothelial Cell Behavior on Vascular Prosthetic Grafts: Effect of Polymer Chemistry, Surface Structure, and Surface Treatment", *ASAIO Journal*, 1999, pp. 272-280.

Saxena, Vishal et al., "Vacuum-Assisted Closure: Microdeformations of Wounds and Cell Proliferation", *Plastic and Reconstructive Surgery*, Oct. 2004, vol. 114, No. 5, pp. 1086-1096.

Schein, Saadia et al., "The "Sandwich" Technique in the Management of the Open Abdomen", *Br. J. Surgery*, May 1986, vol. 73, No. 5, pp. 369-370.

Svedman, P. et al., "A Dressing System Providing Fluid Supply and Suction Drainage Used for Continuous and Intermittent Irrigation", *Annals of Plastic Surgery*, Aug. 1986, vol. 17, No. 2, pp. 125-132.

Williams, "Benefits and Risk in Tissue Engineering", *Materialstoday*, May 2004, pp. 24-29.

Karamuk, E., et al. "Tissupor: Development of a Structured Wound Dressing Based on a Textile Composite Functionalized by Embroidery Technology", tissupor_kt1.url, published Sep. 2001, downloaded Oct. 6, 2004, Switzerland.

http://www.dressings.org/Dressings/telfa.html, Describes an absorbent dressing with a polyester film with openings to reduce adherence of the dressing, Jan. 15, 2008.

International Search Report and Written Opinion dated Mar. 20, 2008.
Argenta, Vacuum-Assisted Closure: A New Method For Wound Control and Treatment: Clinical Experience, Jun. 1997. 15 Pages.
Arnljots, Irrigation Treatment in Split-Thickness Skin Grafting of Intractable Leg Ulcers, 1985. 3 pages.

Svedman, Irrigation Treatment of Leg Ulcers, Sep. 1983. 3 Pages.
Supplementary European Search Report for EP 07 81 0241 completed Oct. 20, 2010.

* cited by examiner

GROWTH STIMULATING WOUND DRESSING WITH IMPROVED CONTACT SURFACES

REFERENCE TO RELATED APPLICATIONS

This application is a continuation-in-part of U.S. patent application Ser. No. 10/982,346, filed on Nov. 5, 2004, which claims priority of U.S. Provisional Patent Application No. 60/561,745, filed on Apr. 13, 2004. This application also claims priority of U.S. Provisional Patent Application No. 60/819,146, filed on Jul. 7, 2006.

FIELD OF THE INVENTION

The invention relates to the general field of bandages and other wound covers. More particularly, the invention relates to the field of wound contact devices that are placed in direct contact with a wound under bandages or under sealing covers for use in suction-assisted or negative pressure wound therapy.

BACKGROUND OF THE INVENTION

Wound healing is a basic reparative process. It has been known throughout time that dressing wounds with appropriate materials aids the natural regenerative process. Historically, such materials have been made from cotton fibers such as gauze. These dressings are beneficial to the healing process because they insulate damaged tissue from external contaminants and because they remove potentially deleterious wound exudates.

As science and medicine have advanced, the technology incorporated into wound healing devices has improved substantially. Highly absorbent wound contact devices capable of absorbing many times their weight in liquids are available. Systems that temporarily seal wounds and utilize suction to remove exudates have found widespread utilization. Devices incorporating anti-microbial agents and biologic healing agents are common. Devices that provide a moist wound environment for improved healing have been found to be useful.

Nevertheless, many common conventional and state-of-the-art wound contact devices have shortcomings, particular for use in suction wound therapy. In an example, gauze and other similar flat fabric materials are commonly used in wound dressings. When gauze in contact with a wound becomes wet with wound exudates, it becomes soggy and soft, losing any structure it may have had and leaving little or no space above the wound surface for new tissue growth to occur. When suction is applied to a gauze wound dressing, the dressing is compressed into a flattened state and any space between the gauze fibers is effectively eliminated. Additionally, even when wound exudates are being removed by suction from a gauze dressing, the gauze remains saturated and pressed against the wound, leaving no space above the wound and thus inhibiting new tissue growth.

In another example, a dressing using a foam material in contact with the wound retains only a minimal amount of small pores at the wound contact surface when suction is applied to the dressing. When a foam dressing is used with suction, the pores of the foam collapse, eliminating space above the wound surface. Absent significant open space above the wound surface, new tissue grows into the foam. Routine removal of the foam dressing causes disruption of new tissue, excessive bleeding, and unnecessary discomfort to the patient. In-growth of tissue into foam is a significant problem because the tissue has nowhere to grow but into the collapsed cell or pore structure of the foam.

In another example, a dressing using a wound contact device in the form of a relatively rigid perforated sheet, such as an Aquaplast sheet, as a substrate in contact with the wound, is not sufficiently flexible and conformable to comfortably and adequately conform to wound surfaces that are often irregular in contour. A dressing having such an inflexible or rigid structured material or wound contact layer causes unnecessary pain and discomfort in a patient. In addition, an Aquaplast or similar sheet is constructed from solid plastic with large holes punched into the plastic. Such a sheet does not have small interconnecting interstices that facilitate the transport of liquid wound exudates away from the surface of the wound. The holes in the Aquaplast sheet simply create reservoirs where deleterious wound exudates can pool and impede wound healing. Because these large holes do not fluidically communicate with each other, fluid removal is not practical. In addition, an Aquaplast sheet does not provide any wicking for the effective removal of wound exudates. Further, an Aquaplast sheet is not permeable to either gas or liquids, and thus does not permit a wound to breath in the places where the sheet material is in contact with the wound surface, nor does it enable efficient transport of fluids and wound exudates away from the wound.

A wound dressing for use in suction wound therapy preferably has some or all of the following characteristics and properties: the dressing should be flexible and conformable to the wound, the dressing should effectively enable transport of wound exudates away from the wound surface, and the dressing should allow sufficient voids above the wound when suction is applied for unobstructed new tissue growth. The dressing should maintain structural integrity when moist and should have a geometry to actively encourage tissue growth. When used in the later stages of tissue regeneration, the dressing should inhibit or minimize entanglement of healthy new tissue into the dressing material. Early in the treatment of some wounds, there may be necrotic or dead tissue in the wound. This dead tissue can be a source of nourishment for deleterious bacteria. A dressing for treating such wounds may have a wound contact surface adapted to debride or remove dead tissue out of the wound.

As described in U.S. patent application Ser. No. 10/982, 346, commonly assigned with this application and from which this application is a continuation in part, wound dressings and wound contact devices have been developed to replace traditional gauze or foam pads under wound bandages or wound sealing covers used in suction assisted wound healing. The goal has been to enhance the healing process though the properties and geometries of wound contact devices.

One such wound contact device comprises a permeable material having a plurality of dimple voids formed in the wound contact side of the device, wherein the dimple voids are preferably disposed in a randomly spaced pattern. Because the contact device comprises a permeable material with interconnecting interstices, it can effectively transport deleterious wound exudates away from the wound surface. The device can be cut to size for a wound, and the cut piece placed in contact with the tissue of the wound under a bandage or under a sealing cover. The dimple voids provide empty space into which new tissue can grow without becoming excessively intertwined with the permeable material, in contrast to the intertwining growth that is known to occur with porous foam pads. The contact elements between the dimple voids provide a main tissue contact surface. The permeable material of the contact device provides sufficient resistance to compression to keep the dimple voids from entirely collapsing when suction or other compacting pressure is applied to the wound dressing. Additionally, the contact device maintains the dimple voids in the presence of moisture.

In addition to providing empty growth space, the combination of the dimple voids and the contact elements imposes a beneficial strain on the tissue when suction is applied to the wound dressing, pulling the tissue into a catenary-like shape within the voids. These forces and the resulting strain imposed on the tissue are believed to stimulate new tissue growth more effectively than the forces obtained in suction therapy using wound dressings that have generally flat surfaces when suction is applied.

It would be advantageous to provide an improved wound contact device comprising a permeable structured material and a wound contact layer affixed to a side of the structured material forming a wound contact surface, with a plurality of voids extending through the contact layer to a depth within the structured material and defining wound contact elements on the wound contact surface. In one embodiment, it would be advantageous to provide a wound contact device having a wound contact surface adapted to prevent healthy tissue growth from becoming entangled with the device. In another example, it would be advantageous to provide a wound contact device having a wound contact surface adapted to debride dead tissue out of a wound so that revascularized healthy tissue can grow. The nature of these improvements and the benefits they confer will be apparent from the description and sample embodiments which appear below.

BRIEF SUMMARY OF THE INVENTION

The present invention provides a wound contact device for use in a wound dressing. The device is particularly adapted for use in a dressing where suction or negative pressure therapy is used to promote healing. The wound contact device comprises a permeable material having a wound contact surface, the wound contact surface comprising a plurality of depressions and/or voids interposed between a plurality of wound contact elements. The material may include a plurality of fibers coupled to one another. The material may alternatively include a polyester felt material.

An embodiment of the present invention provides a wound contact device comprising a thin film affixed to the permeable material for forming the wound contact surface, the thin film covering the wound contact elements and having apertures corresponding to the depressions or voids, the thin film being essentially smooth (i.e., having essentially no surface gaps) so as to resist entanglement with new tissue growth. Another embodiment of the present invention provides a wound contact device comprising a thin fabric layer affixed to the permeable material for forming the wound contact surface, the fabric layer covering the wound contact elements and having apertures corresponding to the depressions or voids, the fabric layer having small gaps or openings so as to enable entanglement with and debriding of necrotic tissue, the openings being smaller than the voids in the wound contact device.

These and other aspects and objects will become apparent from the following description.

BRIEF DESCRIPTION OF THE DRAWINGS

The accompanying drawings, which are incorporated herein and constitute a part of this specification, illustrate preferred embodiments of the invention, and together with the general description given above and the detailed description given below, serve to explain features of the invention.

DETAILED DESCRIPTION OF THE INVENTION

Figure 1:
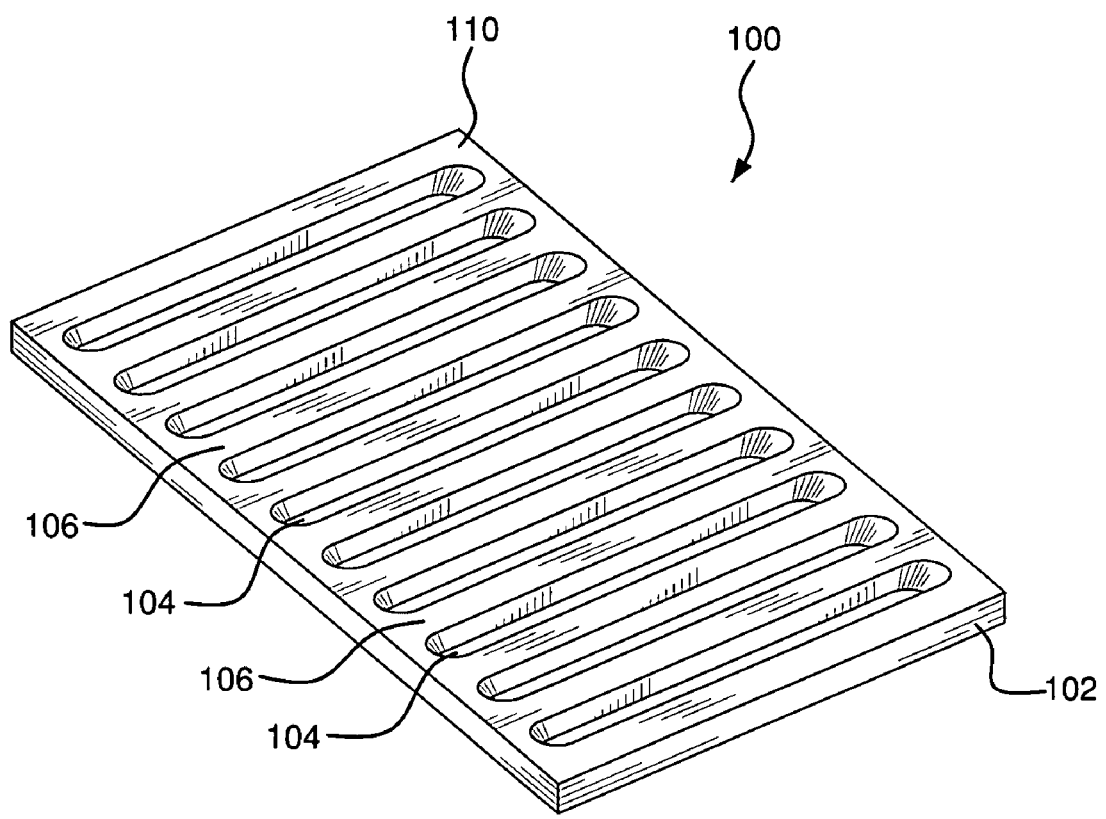
FIG. 1 is a perspective view of a channeled wound contact device according to an exemplary embodiment of the present invention.

A wound dressing is provided comprising a wound contact device having a structured material and a discontinuous contact surface or layer for promoting tissue growth. The contact surface or contact layer includes wound contact elements and voids or depressions interposed between the wound contact elements. The structured material maintains the voids when the wound contact device is placed against the wound so that the empty space or void volume within the voids permits space for tissue growth.

The wound dressing, and in particular the structured material of the wound contact device, is sufficiently physically rugged to resist flattening when forces are imposed to press the wound contact device against the wound surface. Forces pressing the wound contact device against the wound surface include, but are not limited to, suction applied to the wound dressing during application of negative pressure wound therapy. In addition, the material of the wound contact device, and in particular the, structured material, retains its structure when exposed to aqueous or other bodily fluids, in contrast to many traditional wound contact device materials that soften and lose their geometric form as they moisten.

The structured material of the wound contact device is permeable, allowing the communication of suction proximal to the wound surface and allowing for fluids to be drawn from the wound. The structured material can be absorbent, but is able to retain its structure and resist change in the presence of moisture and aqueous liquids.

The voids preferably extend into the structured material to a depth of at least 0.1 mm above the wound surface when the wound contact device is placed against the surface of the wound. More preferably, the depth of the voids is between about 0.2 mm to about 5 mm. The width of the voids, as defined by the empty space between contact elements adjacent to the voids, is preferably greater than 0.1 mm. More preferably, the width of the voids is between about 0.5 mm to about 10 mm. The voids may be of any cross-sectional shape, including oblong, round, irregular, or square, as shown for example in FIGS. 1A, 3A, 5A, and 8, respectively. In addition, the wound contact elements can be pedestals such that the voids intersect or are interconnected to form a shape complementary to the pedestal contact elements, as shown for example in FIG. 7.

Wound healing is recognized as a complex process. When a wound dressing or wound contact device having interposed wound contact elements and voids, as described herein, is forced against a wound surface, a number of biological processes are believed to occur, particularly when the wound dressing is subjected to suction. In suction wound therapy with a wound contact device or wound dressing as described herein, mechanical strain is applied to the underlying tissue. Suction in combination with apertures in the wound contact surface of the wound contact device impose a force resulting in a catenary shape on the tissue, whereby tissue is stretched partially into the voids between the contact elements. The stretched tissue and cells are under strain, which is known to produce cellular proliferation and migration. Growth of new granular tissue is further encouraged by removal of excess fluid exudates away from the wound surface by suction. Periodic replacement of the wound contact device with another wound contact device having randomly spaced dimples, so that different portions of the wound are successively in contact with the contact elements and/or exposed to the voids, encourages growth throughout the wound surface.

A fibrous material can be used to form the structured material of the wound contact device, the fibrous material having all the flexibilities provided by the textile arts. Fibrous textiles can be formed into a structure suitable for use in a wound contact device by various methods. Among these methods are knitting, weaving, embroidering, braiding, felting, spunbonding, meltblowing, and meltspinning. Each of these methods can be further adapted to produce a material having a discontinuous surface structure including wound contact elements and void spaces, as described herein. Such structures can be imparted during production of the textile material by, for example, applying molten fibers directly to a mold as in meltblowing. Alternatively, the structures can be formed by working a formed textile material after production by, for example, heat stamping or vacuum forming. Further, fibrous or textile material can be mixed with an adhesive and sprayed onto a textured surface.

The versatility of fibrous textiles also extends to their easy adaptation to composite applications. Individual fiber materials may be varied to optimize a physical parameter such as rigidity or flexibility. Individual fiber materials can also be selected for their known ability to assist in wound healing. Examples of such fiber materials are calcium alginate and collagen. Alternatively, fibers may be treated with known wound healing agents such as hyaluronic acid or antimicrobial silver. The ratio of the fiber materials can be varied to suit the requirements of the wound. According to one desirable aspect of the invention, different fibers with various wound healing properties may be added as desired.

A wound contact device comprising fibers also has the advantage of being somewhat conformable to the wound surface, which is often irregular. Moreover, fibrous textiles can be formed into structures having numerous small interconnected interstices between coupled or intertwined fibers. Such interconnected interstices enable or assist in the transport of deleterious wound exudates away from the wound surface. The number, size, and orientation of interstices can be controlled and optimized depending on the manufacturing method used to produce the fibrous device.

Figure 3A:
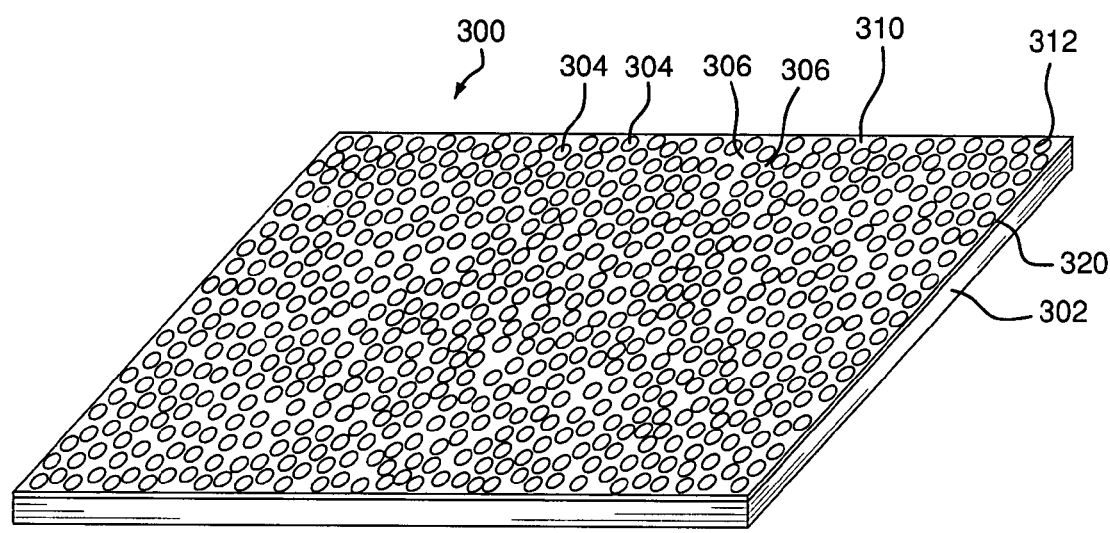
FIG. 3A is a perspective view of a dimpled wound contact device according an exemplary embodiment of the present invention.
Figure 3B:
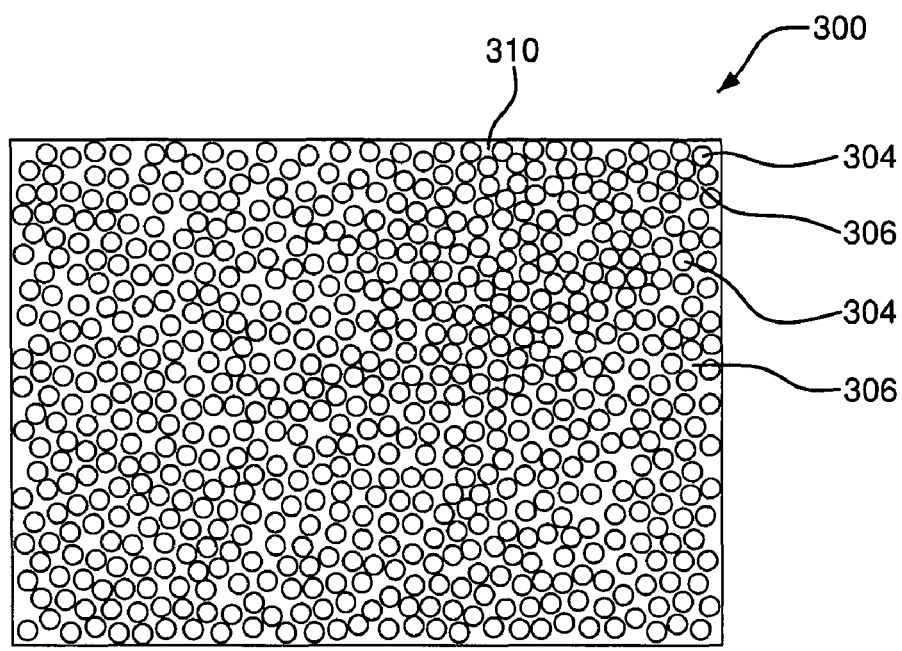
FIG. 3B is a top view of the dimpled wound contact device of FIG. 3A.
Figure 3C:
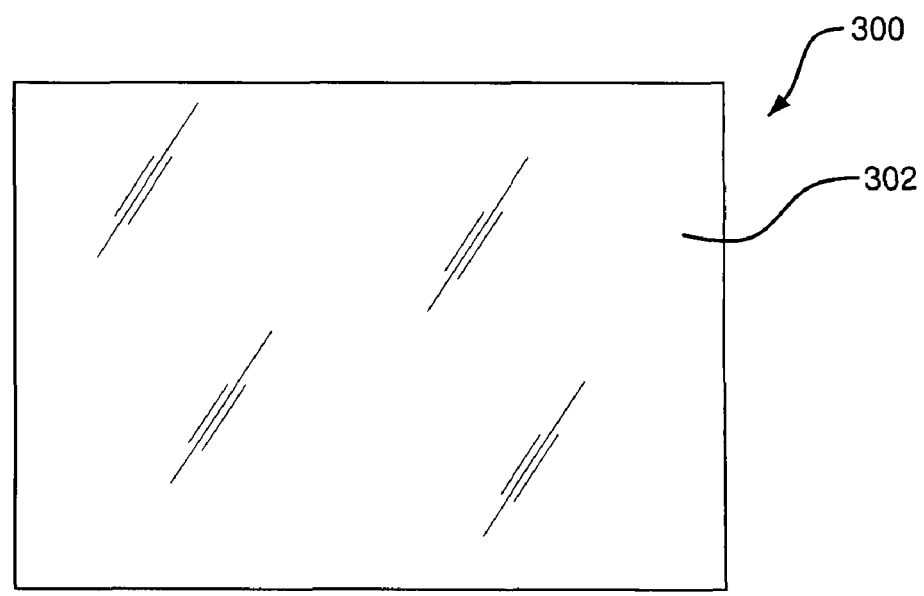
FIG. 3C is a bottom view of the dimpled wound contact device of FIG. 3A.
Figure 3D:
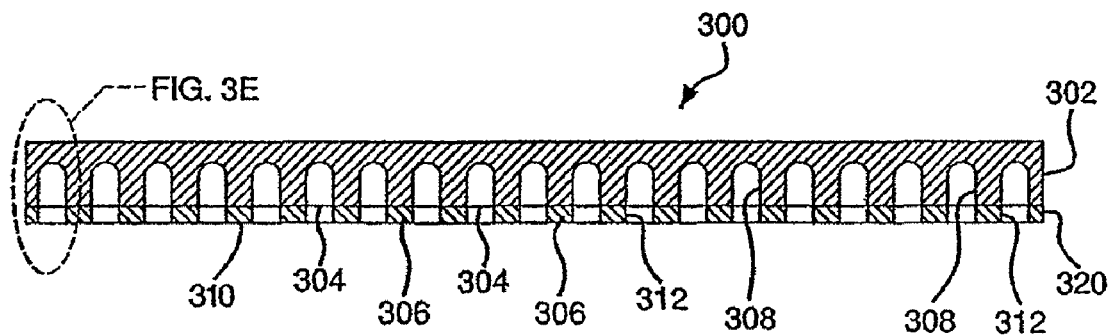
FIG. 3D is a cross sectional view of the dimpled wound contact device of FIG. 3A.
Figure 3E:
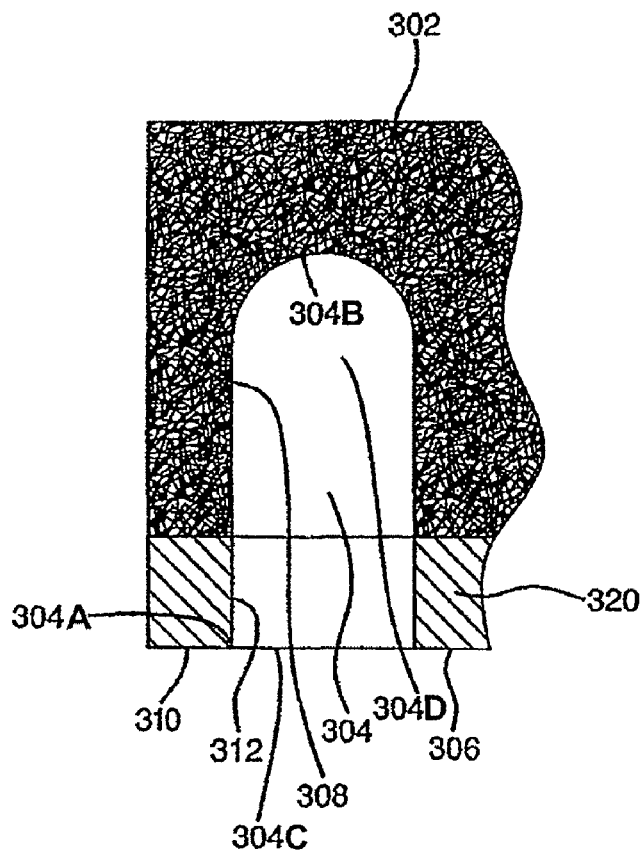
FIG. 3E is an expanded view showing in detail one dimple of the dimpled wound contact device of FIG. 3A.

In an example, such as shown in FIG. 3E, the structured material 302 comprises intertwined fibers defining interstices or interstitial gaps throughout. The interstices provide space for liquids and gases to be suctioned from the wound, thus making the structured material generally permeable. The interstices are smaller than the voids created in the structured material, based on average cross-sectional area or nominal diameter. Usually, the interstices are less than half the size of the voids, and are sometimes much smaller than the voids. In a typical wound contact device 300, as shown in FIGS. 3A to 3E, the voids 304 have a diameter at the wound contact surface 310 in the range of about 1000 microns to about 2000 microns. The voids 304 typically penetrate or extend to a depth in the range of about 250 microns to 1000 microns. In contrast, the interstices or gaps between the fibers through the structured material typically vary from about 0 microns to about 400 microns.

Other fibrous structures that are anticipated as beneficial additions include: (1) fluid absorbing fibers; (2) non-adsorbent fibers; (3) bio-absorbable fibers; (4) wicking fibers to wick fluid away from the surface of the wound; (5) fibers with known healing effects, such as calcium alginate; (6) bio-erodable fibers for the controlled release of a curative agent; (7) conductive fibers for the delivery of an electric charge or current; (8) adherent fibers for the selective removal of undesirable tissues, substances, or microorganisms; and (9) non-adherent fibers for the protection of delicate tissue.

An exemplary embodiment of a wound contact device is illustrated in FIG. 1. A channeled wound contact device 100 comprises a generally conformable structured material 102 and includes a wound contact surface 110. The structured material 102 is preferably made from a polyester material. The polyester material can include a polyester textile such as a felt, knit, weave, or braid. Creep resistance, as exhibited by polyester, is particularly desirable, because it enables the structured material 102 to retain its structure when exposed to moisture and when subjected to compression due to forces including suction applied to the wound dressing. A felt material such as Masterflow RTM manufactured by BBA Group of Wakefield, Mass., has the benefit of interconnecting interstices that facilitate the transport of liquids away from the wound surface. The structured material can further include a polyolefin, such as polyethylene or polypropylene. The structured material can still further include a polyamide such as nylon. The wound contact surface 110 is discontinuous, including void channels 104 interspersed between wound contact elements 106. The void channels 104 extend to a depth into the structured material 102 to provide empty voids into which new tissue can grow. The discontinuities or apertures in the wound contact surface 110 promote the growth of new tissue.

In use, the channeled wound contact device 100 is pressed against a wound into intimate contact with the wound surface. A pressure of 0.1 PSI (5 mm Hg) or more, applied by suction or other means, is desirably applied to press the wound contact surface 110 against the surface of the wound so that the wound contact elements 106 are in intimate contact with injured tissue and the voids 104 remain clear above the wound surface to receive new tissue growth. Preferably, suction is applied in the range of between about 0.25 PSI (12 mm Hg) and about 5 PSI (260 mm Hg). More preferably, suction is applied at a level between about 0.67 PSI (35 mm Hg) and about 1.45 PSI (75 mm Hg).

Figure 2A:
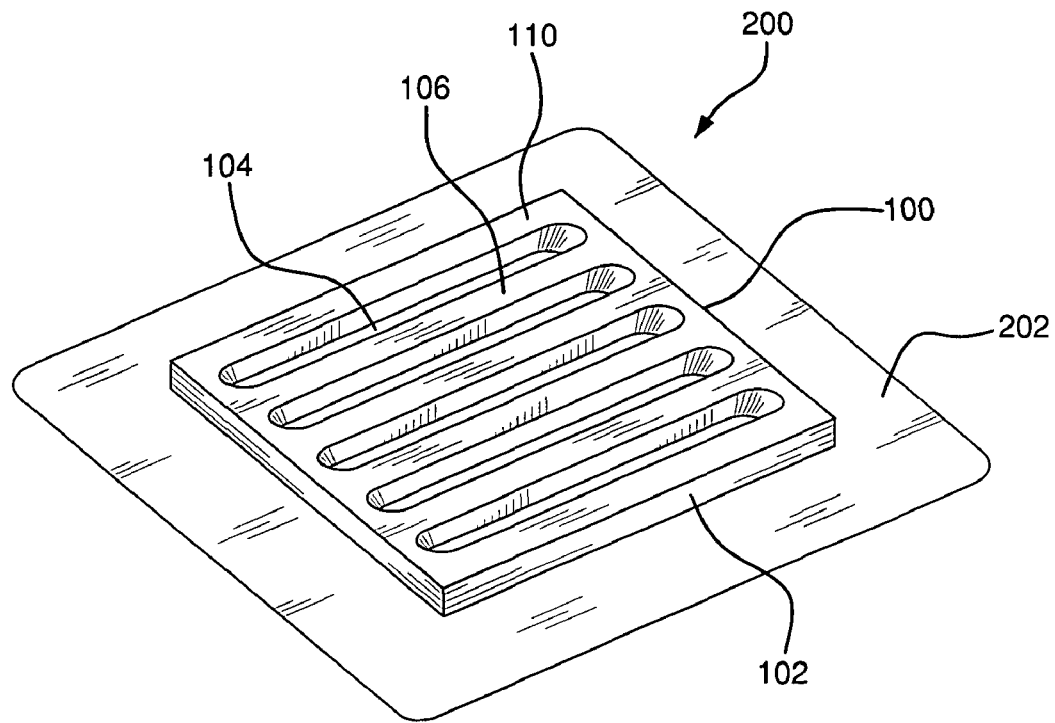
FIG. 2A is a perspective view of a channeled wound contact composite according to an exemplary embodiment of the present invention.
Figure 2B:
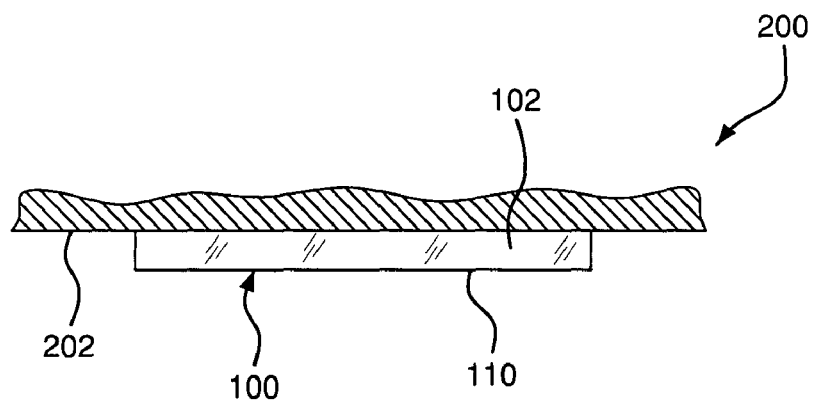
FIG. 2B is a cross section of the channeled wound contact composite of FIG. 2A.

FIGS. 2A and 2B illustrate a wound contact device composite 200 comprising a channeled contact device 100 and a vapor-permeable adhesive-backed sheet 202. Adhesive-backed vapor-permeable sheets, in general, are known in the art and are believed to contribute to wound healing by maintaining a moisture level that is optimal for some wounds. In use, the wound contact device composite 200 is placed onto the surface of the wound with the wound contact surface 110 of the channeled wound contact device 100 in contact with the wound. The adhesive sheet 202 covers the wound contact device 100 and adheres to skin adjacent the wound, securing the contact device 100 in the wound and protecting the wound from bacteria and other external contamination and/or abrasion, while allowing for the transmission of moisture vapor from the wound.

FIGS. 3A to 3E illustrate a dimpled wound contact device 300 comprising a structured material 302 and a wound contact layer 320 having a wound contact surface 310. When the wound contact device 300 is used to treat a wound, the wound contact layer 320 is proximate to the wound and the structured material 302 is disposed distally therefrom. The structured material 302 can be constructed using similar materials and production methods employed with regard to the channeled wound contact device 100. As illustrated in FIG. 3A, the wound contact layer 320 is preferably relatively thin in comparison with the structured material 302. The wound contact layer 320 can be fused or bonded to a side of the underlying material 302. Alternatively, the wound contact layer can be integrally formed with the structured material 302, as shown in FIGS. 9A to 9D. The wound contact layer 320 and the structured material 302 can be made from the same material or from different materials.

As best illustrated in FIGS. 3B, 3D and 3E, the wound contact device comprises a plurality of dimple voids 304 that are generally surrounded by wound contact elements 306. The dimple voids 304 extend through apertures 312 in the contact layer 320 and to a depth in the structured material 302. In particular the voids 304 extend from a first end 304A (FIG. 3E) at the aperture 312 to a second end 304B in the structured material 302, with the first end 304 comprising an open area 304C. Preferably, the dimple voids 304 occupy a total area that is at least about 25% of the total area of the wound contact surface 310. More preferably, the total dimple void area occupies at least about 50% of the total wound contact surface area. The dimple voids 304 are partially defined by sidewalls 308. The sidewalls 308 provide rigidity to help resist compaction of dimple wound contact device 300 under compressive forces created by suction or by securing the wound contact device 300 in contact with the wound. The wound contact elements 306 are generally flat. However, in an embodiment, each wound contact element 306 may be constructed to provide an arcuate contact surface having a radius of contact between about 0.1 mm to about 1 mm.

Dimple voids 304 can be formed in a variety of regular or irregular shapes, such as illustrated in FIGS. 1A, 3A, 5A, 7, and 8. In an embodiment, the voids 304 can be constructed so that they are not "undercut," such that the dimple voids 304 are no larger in nominal diameter or circumference than their corresponding apertures 312. (An undercut void would be characterized by the size of the aperture opening, as measured, e.g., by the diameter or circumference for a generally circular aperture, being smaller than the size of the corresponding inner void. For non-circular apertures and voids, another relevant dimension can be used, such as perimeter or average width.)

In an embodiment, the structured material 302 of the wound contact device 300 is formed from Masterflo RTM. In another embodiment, the structured material 302 is formed from polyester needle felt. The structured material 302 has a thickness in the range of about 1.0 mm to about 1.5 mm. The dimple voids 304 are formed in the material 302, the dimple voids 304 having an average depth of about 0.75 mm and an average diameter of about 2 mm. The dimple voids 304 may be formed into the material 302 prior to attachment of the wound contact layer 320, or the wound contact layer 320 can be attached to the material 302 first and the voids 304 subsequently formed through the wound contact layer 320 (to create the apertures 312) and further into the material 302 (to create the dimple voids 304).

The wound contact device 300 is replaced periodically, usually after being in place on the wound for time periods ranging from several hours to a few days. Because tissue growth preferentially occurs in the regions of the voids 304 compared with the regions of the wound contact elements 306, the dimple voids 304 and wound contact elements 306 of a replacement wound contact device 300 are preferably not positioned to be generally aligned with the regions where the dimple voids 304 and wound contact elements 306 of the previous wound contact device 300 had been. Thus, in order to encourage the generation of new tissue across all regions of the wound, several techniques can be employed to vary the positioning of the dimple voids 304 and contact elements 306 within the wound. In an example, the dimple voids 304 can be arranged randomly so that dimple voids 304 will not be aligned from one portion of wound contact device 300 to another. In another example, wound contact devices 300 can be provided with dimple voids 304 having different diameters, either within the same wound contact device 300 or between successive wound contact devices 300. In yet another example, wound contact devices 300 can be provided with dimple voids 304 having a different spacing, either within the same wound contact device 300 or between successive wound contact devices 300.

As illustrated in FIGS. 3B and 3C, the dimple voids 304 are blinded in the structured material 302, extending only partway through the material 302 from the wound contact surface 310. In a variation of the wound contact device 300, the dimple voids 304 and corresponding contact elements 306 are disposed on both the top and bottom sides of the dimpled wound contact device 300, i.e., the contact device 300 has dimple voids 304 and wound contact elements 306 that are both proximal and distal to the wound surface when the contact device 300 is in contact with a wound. In another variation, some or all of the dimple voids 304 traverse the entire thickness of the structured material 302.

When using the wound contact device 300, the dimple voids 304 can be partially filled with therapeutic substances. For example, antiseptic substances might be placed in voids. 304 for treating infected wounds. Further, biologic healing agents could be delivered in the voids 304 to improve the rate of new tissue formation. Additionally, the wound contact device 300 could have a different function on each side. In an example, one side of the contact device 300 could be optimized for the growth of new tissue, while the other side of the contact device 300 could be optimized for the delivery of anti-microbial agents. In another example, one side of the contact device 300 could have small gaps or roughened areas optimized for debriding necrotic tissue from a wound and the other side of the contact device 300 could have contact elements 306 having a smooth contact surface 310 for preventing entanglement of new tissue growth.

As shown particularly in FIGS. 3A and 3D, the wound contact layer 320 comprises a thin impermeable film attached to a side of the structured material 302 to form a wound contact surface 310 including the wound contact elements 306 and interposed apertures 312 corresponding to the dimple voids 304. The impermeable film is preferably a polyester film made from the resin Polyethylene Terephthalate (PET) such as sold under the trademark Mylar®. Other film materials may be used, including but not limited to silicone, cellulose acetate, vinyl, urethane, or poly lactic acid. The film of the contact layer 320 is relatively thin compared with the permeable material 302 into which the voids 304 extend. Available films having a thickness of less than about 0.020 inches (0.51 millimeters) are generally satisfactory, and films having a thickness of less than about 0.004 inches (0.102 millimeters) are preferred. In an embodiment, a film having a thickness of about 0.0005 inches (0.0127 millimeters) is used. The film has a generally smooth surface with minimal gaps or openings into which tissue can grow and become entangled. Thus, because nearly all tissue growth is into the voids 304, the wound contact device 300 can be pulled off of the wound with very little tissue disruption and with minimal discomfort to the patient.

The wound contact surface 310 comprising the film layer 320 can be made even more releasable from the healing wound tissue by applying a coating, such as a hydrogel, to the wound contact layer 320. In a preferred embodiment, the film is a plastic film and a polymeric hydrogel is cross-linked with the plastic film to form a hydrogel laminate that resists delamination and potential retention of the gel in the wound when the wound contact device 300 is removed and changed. The gel provides the wound contract layer 320 of the contact device 300 with a cool, wet, and slippery contact surface 310 that allows the wound contact device 300 to be removed from the wound with minimal tissue disruption and discomfort.

In an embodiment, the film layer 320 can comprise a dissolvable film. One or more drugs and other agents can be integrated to the dissolvable film. When the film dissolves in the presence of moisture, the drug or agent is released.

Figure 6:
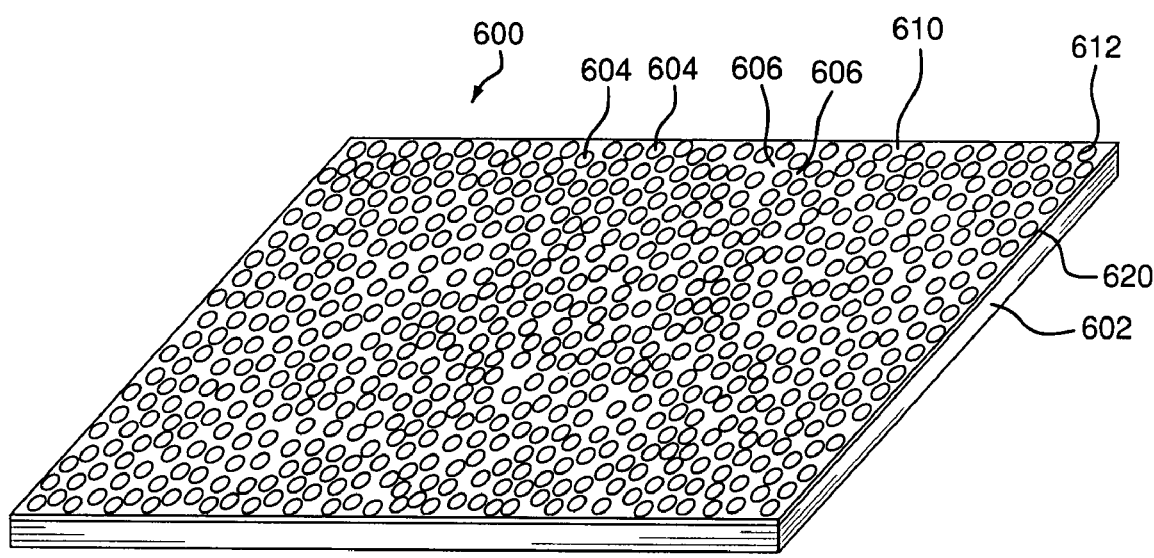
FIG. 6 is a perspective view of a dimpled wound contact device according to an exemplary embodiment of the present invention.

As shown particularly in FIG. 6, a wound contact device 600 comprises a structured material 602 and a wound contact layer 620 on a side of the material 602. The wound contact layer 620 comprises a thin sheet of permeable non-woven fabric attached to the structured material 602 to form a wound contact surface 610 including wound contact elements 606 and interposed apertures 612 corresponding to dimple voids 604 that extend into the material 602. The permeable sheet of fabric is highly calendered by pressing the fabric between rollers or plates to produce a generally uniform or glazed surface having a mean surface roughness with gaps in the range of about 0 microns to about 200 microns. Because it has small surface gaps or roughened areas, a contact device 600 having the contact layer 620 can be advantageously applied in stages of wound healing, when there is a benefit from allowing some tissue intertwining with the wound contact device 600. In particular, necrotic tissue may be found initially in some wounds. Necrotic tissue is preferably debrided out of the wound when the wound contact device is changed. Accordingly, in the early stages of wound healing, dead or necrotic tissue can be removed by providing a contact layer 620 that promotes adherence of such tissue, which is then removed when the wound contact device 600 is taken from the wound. The resulting removal of necrotic tissue encourages more healthy new growth when a fresh wound contact device is applied.

A preferred fabric sheet for forming the contact layer 620 is a spunbonded (non-woven) low-lint 100% polyester fiber fabric, although other synthetic fabrics such as spunbonded polypropylene and spunbonded composite fibers can be highly calendered to sufficiently fine flat surfaces. The fabric preferably has a thickness of less than about 0.020 inches (0.51 millimeters), and more preferably has a thickness of less than about 0.004 inches (0.102 millimeters).

The respective properties of the different contact layers 620 and 320 in early and late stage healing, respectively, make it advantageous to provide a progressive healing kit containing one or more wound contact devices 600 comprising the fabric contact layer 620 having small surface gaps or roughened areas, along with one or more wound contact devices 300 comprising the film contact layer 320 having essentially no surface irregularities or gaps. The wound contact devices in the kit may be used to remove necrotic tissue earlier in the healing process with the contact devices 600 comprising the fabric contact layers 620, and to reduce patient discomfort later in the healing process with the contact devices 300 comprising the film laminate contact layers 320.

Figure 4A:
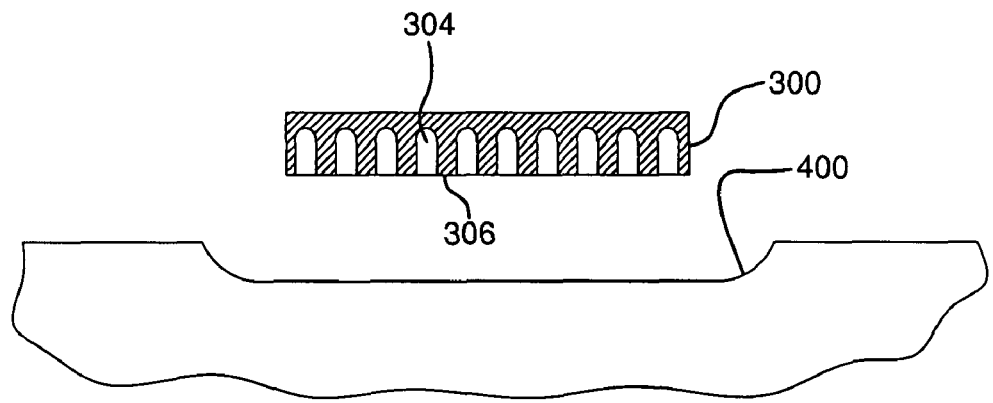
FIGS. 4A, 4B, 4C illustrate a method of using the dimpled wound contact device of FIG. 3A.
Figure 4B:
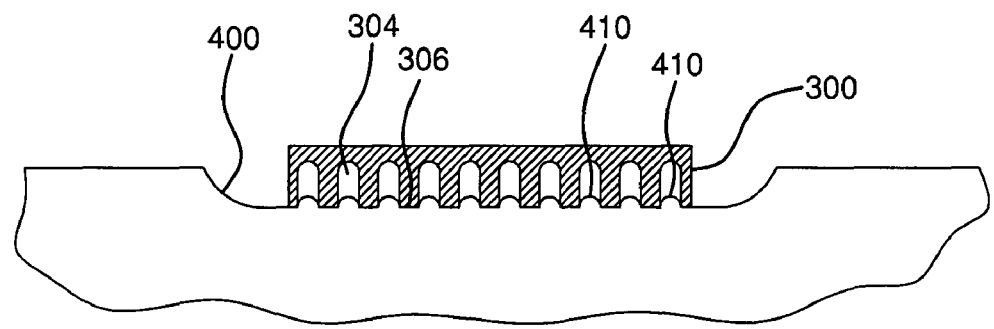
Figure 4C:
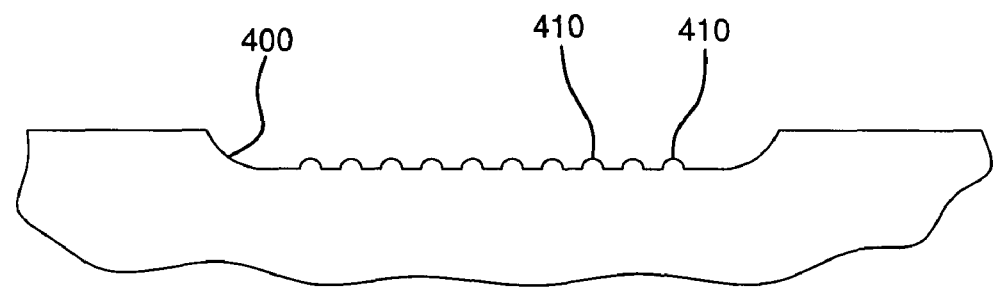

A dimpled contact device, such as the wound contact device 300, is illustrated by FIGS. 4A, 4B, and 4C. In particular, FIG. 4A shows a wound surface 400 prior to application of the wound contact device, FIG. 4B shows the wound surface 400 during application of the wound contact device, and FIG. 4C shows the wound surface after removal of the wound contact device. The wound surface 400 can be a portion of a wound, including, for example, all or most of a shallow surface wound or a small interior portion of a deep tissue wound. As shown in FIG. 4B, the wound contact elements 306 are in intimate contact with the wound surface 400 while new tissue growth 410 protrudes from the wound surface 400 into the dimple voids 302 of the wound contact device 300. The wound contact device 300 can be pressed against the wound surface 400 by suction or other means such as taping the contact device 300 to skin surrounding the wound or wrapping a bandage over the contact device 300 and the affected body part. As shown in FIG. 4C, when the wound contact device 300 is removed, the new tissue growth 410 is left intact.

Figure 5A:
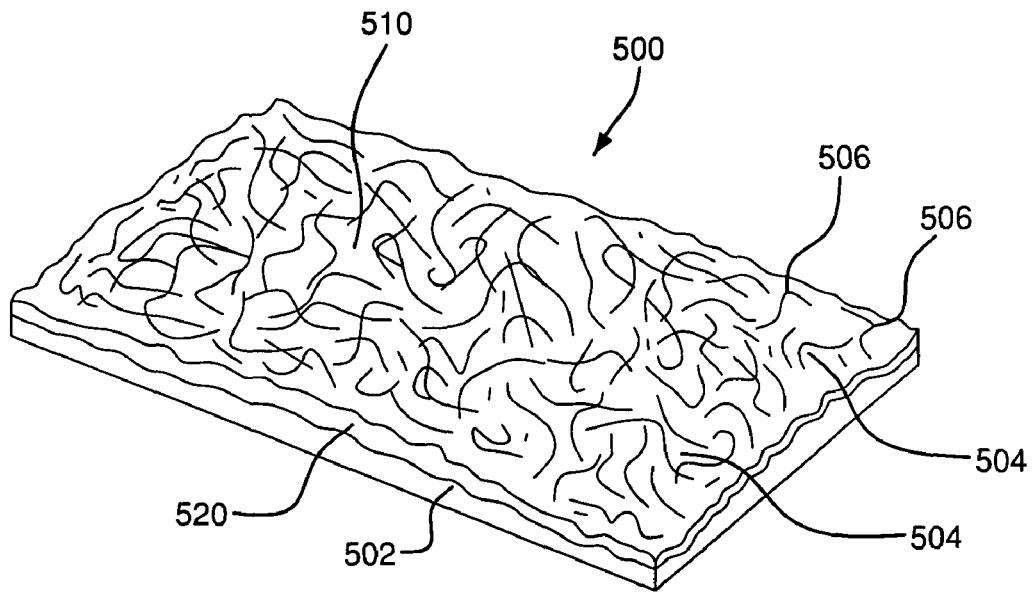
FIG. 5A is a perspective view of an irregular wound contact device according to an exemplary embodiment of the present invention.
Figure 5B:
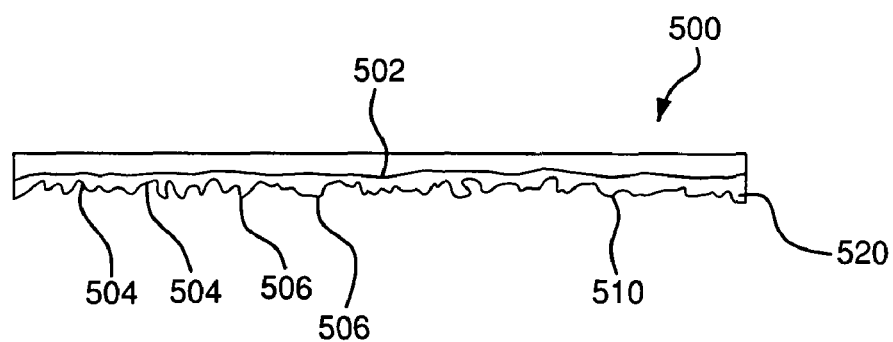
FIG. 5B is a cross sectional view of the irregular wound contact device of FIG. 5A.

As illustrated in FIGS. 5A and 5B, a rough irregular wound contact device 500 comprises a structured material 502 and a roughened wound contact surface 510 including irregular voids 504 interposed with irregular contact elements 506. The irregular contact elements 506 can act as "hook-like" members adapted to contact and stick to necrotic tissue when the contact device 500 is placed in contact with the wound. When the contact device 500 is removed from the wound, the wound is debrided of necrotic tissue, which is stuck to the hook like protrusions 506 and is removed from the wound. Removal of necrotic tissue is an important part of healing wounds because necrotic tissue is a source of nourishment for harmful bacteria.

Even after removal of the necrotic tissue, the wound may still be infected, thus inhibiting healing. The material 502 of the wound contact device 500 can comprise an antimicrobial agent such as antimicrobial silver, which is useful in killing bacteria. Removal of necrotic tissue and the killing of bacteria residing in the wound can help the wound transition to the proliferative phase, when new tissue is formed. Continued use of the wound contact device 500 including an antimicrobial agent can maintain a low bacteria level in the wound and accelerate the healing, encouraging growth and proliferation of new cells and tissue. New cell growth can further be encouraged by addition of other growth enhancing materials to the material 502 of the wound contact device 500.

As shown particularly in FIG. 5B, the irregular wound contact device 500 has a random cross sectional profile of voids 504 and contact elements 506. The material 502 of the contact device 500 may be made from polyester felt or batting. In an embodiment, the felt is singed with hot air so that a percentage of the felt fibers melt to form a textured surface 520 with a number of hook-like elements 506. In another embodiment, the hook-like elements 506 can resemble those typically used in hook and loop fabric fasteners. The roughened surface 510 of the irregular contact device 500 can also be formed by passing the material 502 under convective heat at or about the melting point of the material from which the material 502 is comprised. For example, polyester materials typically melt in a range from about 250° C. to about 290° C. A polyester felt material passed briefly under a convective heat source operating in this temperature range will experience surface melting and subsequent fusing of the polyester strands at its surface. The degree of surface melting can be controlled with temperature and exposure time to yield a surface 510 having a desired roughness exhibiting irregular voids 504 and irregular contact elements 506. Although the irregular contact device 500 is illustrated as having only one roughened surface 510, both the upper and lower surfaces of the contact device 500 may be similarly roughened. A wound contact device 500 having both opposed sides roughened would be useful, for example, in the treatment of an undermined wound.

Figure 7:
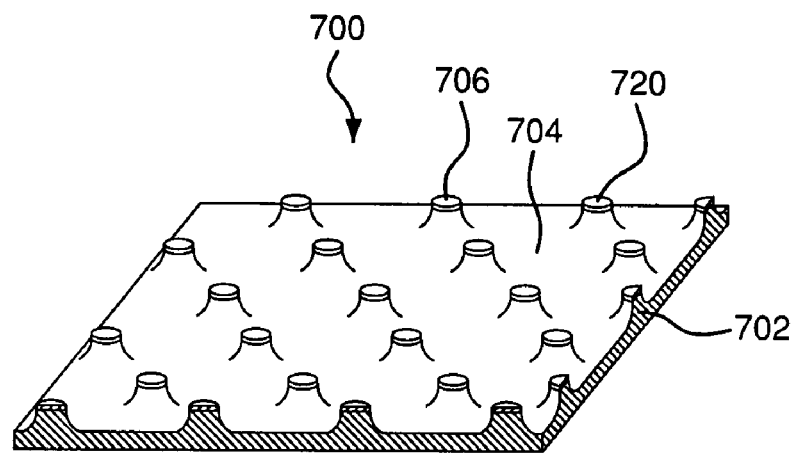
FIG. 7 is a perspective view of a would contact device according to an exemplary embodiment of the present invention.

As illustrated in FIG. 7, a wound contact device 700 comprises a structured material 702 and a plurality of wound contact elements 706 defining void spaces 704, each wound contact element having a wound contact layer 720. When the contact device 700 is placed into a wound, the contact layer 720 of the pedestal-like wound contact elements 706 is in contact with the wound surface, and the void spaces 704 remain clear for tissue growth. The structured material 702 has sufficient resistance to the compressive forces of therapeutic suction to maintain the empty void spaces 704 about the wound surface when suction is applied to the wound. In an embodiment, the wound contact layer 720 comprises a thin film having minimal surface discontinuities or gaps, as described above with reference to the embodiment of FIGS. 3A to 3E. In another embodiment, the wound contact layer 720 comprises a thin sheet of non-woven fabric, as described above with reference to FIGS. 6A to 6D. In yet another embodiment the wound contact layer 720 is integral to and part of the structured material 702.

Figure 8:
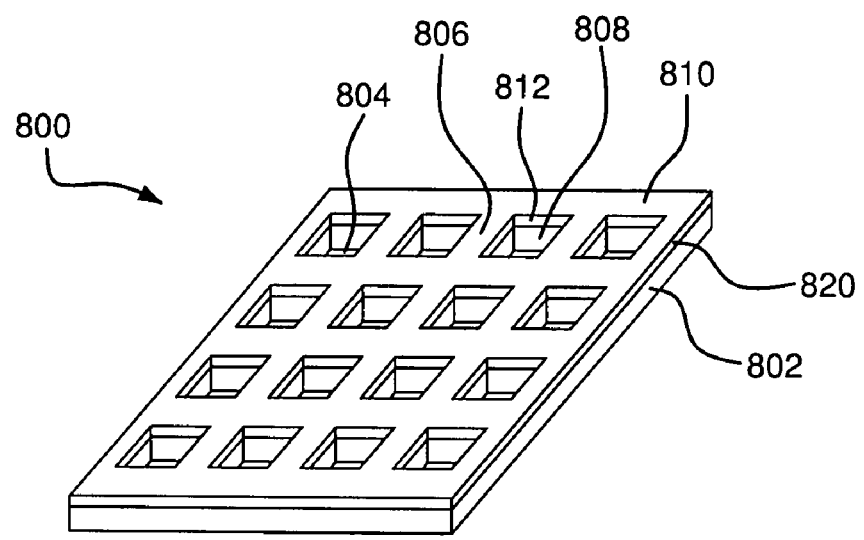
FIG. 8 is a perspective view of a wound contact device according to an exemplary embodiment of the present invention.
Figure 9A:
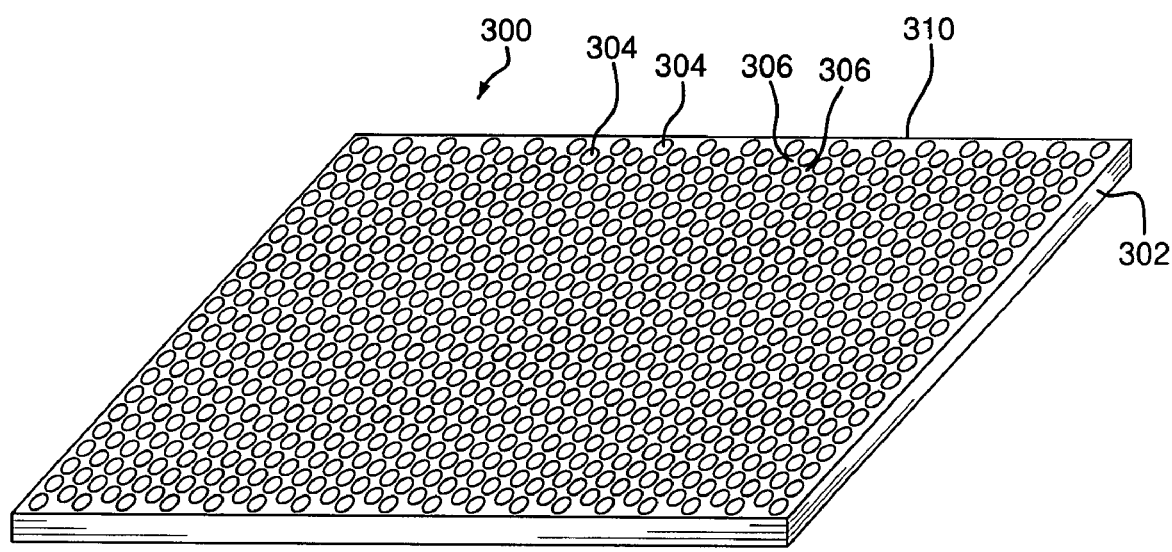
FIG. 9A is a perspective view of a dimpled wound contact device according an exemplary embodiment of the present invention.
Figure 9B:
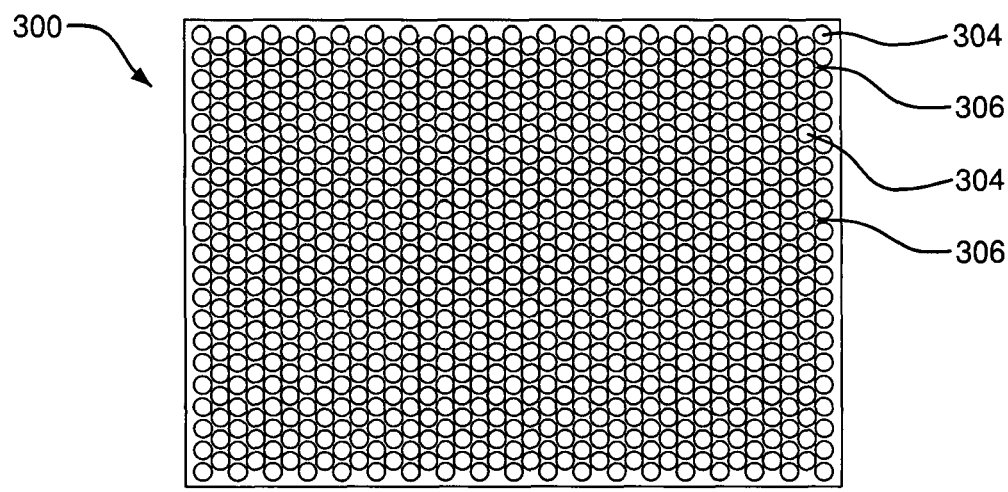
FIG. 9B is a top view of the dimpled wound contact device of FIG. 9A.
Figure 9C:
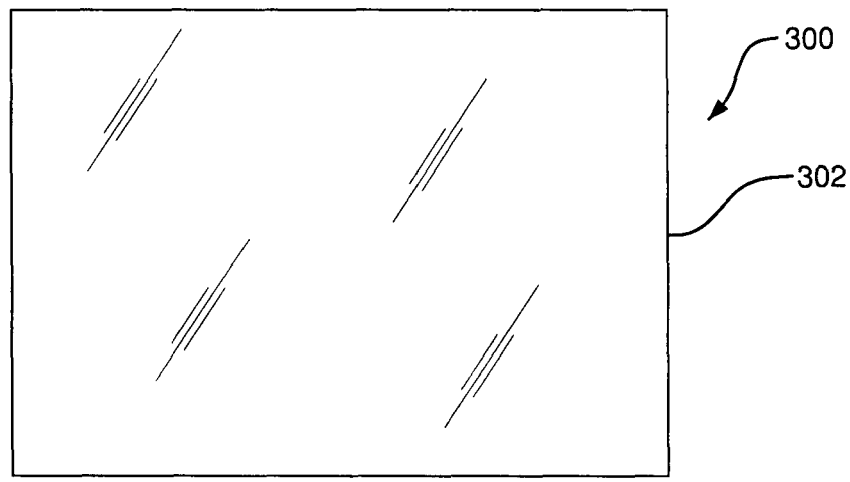
FIG. 9C is a bottom view of the dimpled wound contact device of FIG. 9A.
Figure 9D:
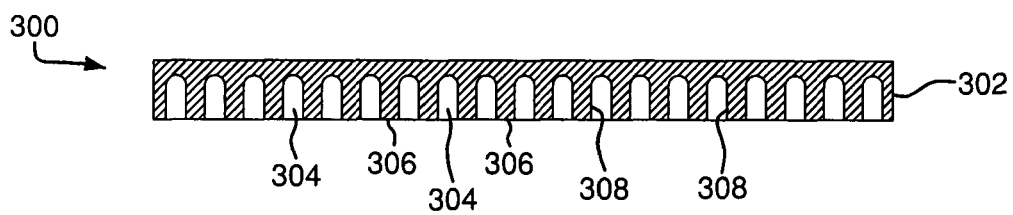
FIG. 9D is a cross sectional view of the dimpled wound contact device of FIG. 9A.

As illustrated in FIG. 8, a wound contact device 800 comprises a structured material 802 having a plurality of generally square or rectangular voids 804 and a wound contact surface 810 comprising wound contact elements 806. The wound contact surface 810 can be formed from a wound contact layer 812.

Treatment with a wound contact device as described herein is most effective when the contact device is held in intimate contact with the wound surface. The contact device is preferably held with a pressure of at least about 0.1 PSI (5 mm Hg). Typically, the wound area is sealed with a conformable cover and suction is applied to the dressing under the cover. The dimpled wound contact device 300 is particularly well-adapted for application of suction, because the material 302 is adapted to retain its structure, including the voids 304 so as to maintain empty space therein, under the compressive force of suction and in the presence of moisture and other wound exudates. The wound contact device 300 is disposed in the wound such that the wound contact surface 310 is in contact with the wound surface and the voids 304 are open above the wound surface, as generally depicted in FIG. 4B. Typically, suction is applied at a level ranging between about 0.25 PSI (12 mm Hg) and about 5 PSI (260 mm Hg). Preferably, suction is applied at a level between about 0.67 PSI (35 mm Hg) and about 1.45 PSI (75 mm Hg). The effectiveness of suction can be further improved by applying a wound packing material to the back of the wound contact device as part of the wound dressing. One such suitable wound packing material is described in U.S. patent application Ser. No. 10/981,119, filed on Nov. 4, 2004.

Case Study 1

Patient A is a 70 year old male with a Stage IV decubitus ulcer on the right hip with significant undermining. A wound contact device including the structured material and wound contact surface of the present invention was applied to the wound and an adhesive film was placed over the wound and the wound contact device. A suction of about 1.1 PSI was applied beneath the adhesive film to impart a force upon the wound. The suction was maintained substantially continuously. The wound contact device was replaced every two to four days. After use of the wound contact device for 30 days, the undermined portion of the wound had virtually healed and the area of the wound opening had decreased from 66 square centimeters to 45 square centimeters. A split thickness skin graft was applied to the wound.

Case Study 2

Patient B is a 50 year old male with a facture of the right ankle with exposed bone. A plate was used to reduce the fracture and a rectus abdominus free flap was performed to cover the exposed bone and hardware. The flap only partially survived resulting in an open wound with exposed bone and hardware. A wound contact device of the present invention was applied to the wound and an adhesive film was placed over the wound and the contact device. A force was applied to the contact structure by the application of an ace bandage wrapped around the ankle and/or by the application of suction. The suction force was generally applied for about half of the day and the force of the bandage wrap was maintained for the remainder of the day. For a number of days, the bandage wrap was solely used to impart the force. When the force was imparted by suction, a suction of between about 1 PSI and about 2 PSI was used. In less than 2 weeks, new tissue had grown over the exposed hardware. Within 7 weeks, the wound area was reduced from 50 square centimeters to 28 square centimeters.

While preferred embodiments of the invention have been shown and described herein, it will be understood that such embodiments are provided by way of example only. Numerous variations, changes, and substitutions will occur to those skilled in the art without departing from the spirit of the invention. Accordingly, it is intended that the appended claims cover all such variations as fall within the spirit and scope of the invention.

We claim:

1. A wound contact device for use in treating a wound with suction to encourage cellular activity at the wound to facilitate wound healing, the wound contact device comprising a permeable material and a wound contact layer, the permeable material having a plurality of interstices, the wound contact layer comprising a thin film formed of a material that is resistant to adhering to the wound, the thin film forming a wound contact surface arranged to directly engage the wound, but not adhere to the wound, the wound contact device having a plurality of voids extending from the wound contact surface through the wound contact layer into the permeable material, each of the voids having a depth in the range of 0.2 mm to 5 mm and comprising a first end, a second end and a sidewall located between the first and second ends, the first end comprising an open area at the contact surface, the second end being located within the permeable material, the sidewall of each of the voids forming the boundary of an open space from the first end of the void to the second end of the void, the open space being open at all times irrespective of whether or not suction is applied to the wound contact device, a portion of the sidewall of each of the voids within the permeable material being bounded by some of the interstices, the voids defining wound contact elements on the wound contact surface, the sidewalls of the voids being resistant to collapse to maintain empty space in the voids when exposed to moisture and other wound exudates and the application of continuous suction within the range of 0.67 PSI to 1.45 PSI to the wound contact device to enable tissue at the voids to be readily drawn into the empty space by the application of such suction, whereupon a mechanical force is applied to the tissue at the voids to stretch that tissue in the empty space to result in strain on that tissue to encourage cellular activity and tissue growth.

2. The wound contact device of claim 1, wherein the thin film comprises a thin plastic sheet.

3. The wound contact device of claim 1, wherein the thin film comprises a film chosen from the group consisting of polyester film, cellulose acetate film, and vinyl film.

4. The wound contact device of claim 3, wherein the polyester film is made from polyethylene terephthalate.

5. The wound contact device of claim 1, wherein the thickness of the thin film is less than 0.020 inches (0.51 millimeters).

6. The wound contact device of claim 5, wherein the thickness of the thin film is less than 0.004 inches (0.102 millimeters).

7. The wound contact device of claim 6, wherein the thickness of the thin film is 0.0005 inches (0.0127 millimeters).

8. The wound contact device of claim 1, further comprising a coating on the wound contact surface of the wound contact layer.

9. The wound contact device of claim 8, wherein the coating is a hydrogel coating.

10. The wound contact device of claim 9, wherein the hydrogel coating is cross-linked to the wound contact layer.

11. A wound dressing for treating a wound with suction to encourage cellular activity at the wound to facilitate wound healing, the wound dressing comprising a permeable material having interconnected interstices for transporting fluid away from the wound and a wound contact surface, the wound contact surface comprising a thin film formed of a material that is resistant to adhering to the wound and being arranged to directly engage the wound, but not adhering to the wound, the wound contact surface having a plurality of voids, each of the voids extending from the wound contact surface into the permeable material, each of the voids having a depth in the range of 0.2 mm to 5 mm and comprising a first end, a second end and a sidewall located between the first and second ends, the first end comprising an open area at the wound contact surface, the second end being located within the permeable material, the sidewall of each of the voids forming the boundary of an open space from the first end of the void to the second end of the void, the open space being open at all times irrespective of whether or not suction is applied to the wound dressing, a portion of the sidewall of each of the voids within the permeable material being bounded by some of the interstices, the sidewalls of the voids of the wound dressing being resistant to collapse to maintain empty space in the voids when exposed to moisture and other wound exudates and the application of continuous suction within the range of 0.67 PSI to 1.45 PSI to the wound dressing to enable tissue at the voids to be readily drawn into the empty space by the application of such suction, whereupon a mechanical force is applied to the tissue at the voids to stretch that tissue in the empty space to result in strain on that tissue to encourage cellular activity and tissue growth.

12. The wound dressing claim 11, wherein the wound dressing comprises synthetic fibers and the interconnected interstices are disposed between the fibers.

13. The wound dressing of claim 11, wherein the average size of the voids is greater than the average size of the interstices.

14. The wound dressing of claim 13, wherein the average size of the voids is twice the average size of the interstices.

15. The wound dressing of claim 11, wherein the average size of the interstices between the fibers is less than 400 microns and the average diameter of the voids is greater than 1000 microns.

16. The wound dressing of claim 11, wherein the wound contact surface is impermeable between the voids.

17. A flexible, conformable wound contact device for use in treating a wound with suction to encourage cellular activity at the wound to facilitate wound healing, the wound contact device comprising a permeable material and a wound contact layer on the permeable material, the permeable material comprising a plurality of interconnected interstices, the wound contact layer comprising a thin, substantially impermeable film formed of a material that is resistant to adhering to the wound and being arranged to directly engage the wound, but not adhere to the wound, the film forming a wound contact surface, the wound contact device having a plurality of discrete voids extending from the wound contact surface through the wound contact layer into the permeable material, each of the voids having a depth in the range of 0.2 mm to 5 mm and comprising a first end, a second end and a sidewall located between the first and second ends, the first end comprising an open area at the contact surface, the second end being located within the permeable material, the sidewall of each of the voids forming the boundary of an open space from the first end of the void to the second end of the void, the open space being open at all times irrespective of whether or not suction is applied to the wound contact device, a portion of the sidewall each of the voids within the permeable material being bounded by some of the interstices, the voids having a width of at least 0.1 mm and defining at least 25% of the wound contact surface, the voids being in fluid communication with a plurality of the interstices, the sidewalls of the voids being resistant to collapse to maintain empty space in the voids when exposed to moisture and other wound exudates and the application of continuous suction within the range of 0.67 PSI to 1.45 PSI to the wound contact device to enable tissue at the voids to be readily drawn into the empty space by the application of such suction, whereupon a mechanical force is applied to the tissue at the voids to stretch that tissue in the empty space to result in strain on that tissue to encourage cellular activity and tissue growth.

18. The wound contact device of claim 17 wherein some of the interstices are located between immediately adjacent voids.

19. The wound contact device of claim 17 wherein each of said voids includes a permeable sidewall.

20. The wound contact device of claim 19 wherein some of the interstices are located between immediately adjacent voids and are in fluid communication with the permeable sidewalls of those voids.

21. The wound contact device of claim 17 wherein the permeable material comprises a plurality of fibers coupled together, the coupled fibers defining a plurality of the interstices between the fibers.

22. The wound contact device of claim 20 wherein the permeable material comprises a plurality of fibers coupled together, the coupled fibers defining a plurality of the interstices between the fibers.

23. The wound contact device of claim 17 wherein the film is smooth to resist entanglement with new tissue growth.

24. The wound contact device of claim 17 wherein the interstices are smaller that the voids.

25. The wound contact device of claim 23 wherein the interstices are less than half the size of the voids.

26. The wound contact device of claim 17 wherein the voids are resistant to collapse at suction levels between 0.25 psi and 5 psi.

27. The wound contact device of claim 1 wherein each of the voids forms a continuously shaped passageway therethrough from the wound contact surface to the permeable material.

28. The wound contact device of claim 1 wherein each of the voids has a generally uniform cross-sectional area from the wound contact surface to the permeable material.

29. The wound contact device of claim 1 wherein each of the voids has the same cross-sectional shape from the wound contact surface to the permeable material.

30. The wound contact device of claim 1 wherein the cross-sectional area of each of the interstices that bound the portion of the sidewall of each void is smaller than the cross-sectional area of the portion of the void extending into the permeable material.

31. The wound dressing of claim 11 wherein each of the voids forms a continuously shaped passageway therethrough from the wound contact surface to the permeable material.

32. The wound dressing of claim 11 wherein each of the voids has a generally uniform cross-sectional area from the wound contact surface to the permeable material.

33. The wound dressing of claim 11 wherein each of the voids has the same cross-sectional shape from the wound contact surface to the permeable material.

34. The wound dressing of claim 11 wherein the cross-sectional area of each of the interstices that bound the portion of the sidewall of each void is smaller than the cross-sectional area of the portion of the void extending into the permeable material.

35. The wound contact device of claim 17 wherein each of the voids forms a continuously shaped passageway therethrough from the wound contact surface to the permeable material.

36. The wound contact device of claim 17 wherein each of the voids has a generally uniform cross-sectional area from the wound contact surface to the permeable material.

37. The wound contact device of claim 17 wherein each of the voids has the same cross-sectional shape from the wound contact surface to the permeable material.

38. The wound contact device of claim 17 wherein the cross-sectional area of each of the interstices that bound the portion of the sidewall of each void is smaller than the cross-sectional area of the portion of the void extending into the permeable material.

\* \* \* \* \*